US006143876A

United States Patent [19]
Gershoni

[11] Patent Number: 6,143,876
[45] Date of Patent: Nov. 7, 2000

[54] ANTIBODIES DIRECTED AGAINST BINDING-ASSOCIATED EPITOPES

[75] Inventor: Jonathan M. Gershoni, Rehovot, Israel

[73] Assignee: Ramot University Authority for Applied Research and Industrial Development Ltd., Israel

[21] Appl. No.: 09/433,420

[22] Filed: Nov. 4, 1999

Related U.S. Application Data

[62] Division of application No. 09/235,592, Jan. 22, 1999, which is a continuation of application No. 08/464,726, filed as application No. PCT/US93/12639, Dec. 29, 1993, Pat. No. 5,925,741.

[30] Foreign Application Priority Data

Dec. 31, 1992 [IL] Israel ........................................ 104291
Feb. 17, 1993 [IL] Israel ........................................ 104767

[51] Int. Cl.$^7$ ........................... C07K 16/00; A61K 39/42
[52] U.S. Cl. ................................. 530/388.35; 530/391.3; 530/391.7; 424/160.1
[58] Field of Search ........................... 530/388.35, 391.3, 530/391.7; 424/160.1

[56] References Cited

PUBLICATIONS

*The Faseb Journal*, vol. 7, No. 12, issued Sep. 1993, Gershoni et al., "HIV binding to its receptor creates specific epitopes for the CD4/gp 120 complex," pp. 1185–1187.

*Journal Of Experimental Medicine*, vol. 172, issued Oct. 1990, Caleda et al., "Antibody raised against soluble CD4–rgp 120 complex recognizes the CD4 moiety and blocks membrane fusion without inhibiting CD4–gp 120 binding," pp. 1143–1150.

*Parasitology*, vol. 88, issued 1984, Ortega et al., The occurrence of antibodies to hidden and exposed determinants of surface antigens of Trichinella spiralis, pp. 359–369.

Abstract 586686, *Journal of Laboratory Clinical Medicine*, vol. 86, No. 5, issued 1975, Javid et al., "The modification of hemoglobin antihemiglobin reaction by haptoglobin," pp. 777–784.

Abstract 6538081, *British Journal of Haematology*, vol. 68, No. 3, issued 1988, Nordfang et al., "Radioimmunoassay afor quantitative measurement of Factor VIII–heavy chain," pp. 307–312.

Abstract 207470, *Scandinavian Journal of Immunology*, vol. 3, No. 2, issued 1974, Lind et al., Immunochemical study of the interaction between staphylococcal protein A, rabbit antistaphyloccoccal sera, and selected sera from nonimmunized animals, pp. 147–156.

Abstract 407661, *Scandinavian Journal of Immunology*, vol. 3, No. 6, issued 1974, Lind., I., "The formation of antibodies against hidden determinants of autologous IgG during immunization of rabbits with Staphylococcus aureus," pp. 689–696.

Abstract 359023, *International Journal of Parasitology*, vol. 4, No. 6, issued 1974, Boreham et al., "Autoimmunity in trypansome infections II. Anti fibrin/fibrinogen (anti–F) autoantibody in Trypanosoma (Trypanozoon) brucei infections of the rabbit," pp. 601–607.

Abstract 9626985, *Journal of Immunology*, vol. 149, No. 6, issued 1992, Callahan et al., "Analysis of HIV–induced autoantibodies to cryptic epitopes on human CD4," pp. 2194–2202.

*Primary Examiner*—Hankyel Park
*Attorney, Agent, or Firm*—Ostrolenk, Faber, Gerb, & Soffen, LLP

[57] ABSTRACT

Binding of two members of a binding couple reveals epitopes which are revealed only after binding and the monoclonal antibody secreted from the hybridoma cell line CG-10 directed against these epitopes bind to the bound couple at a significantly higher affinity than their binding affinity to either of the two members themselves when not bound to one another.

10 Claims, 9 Drawing Sheets

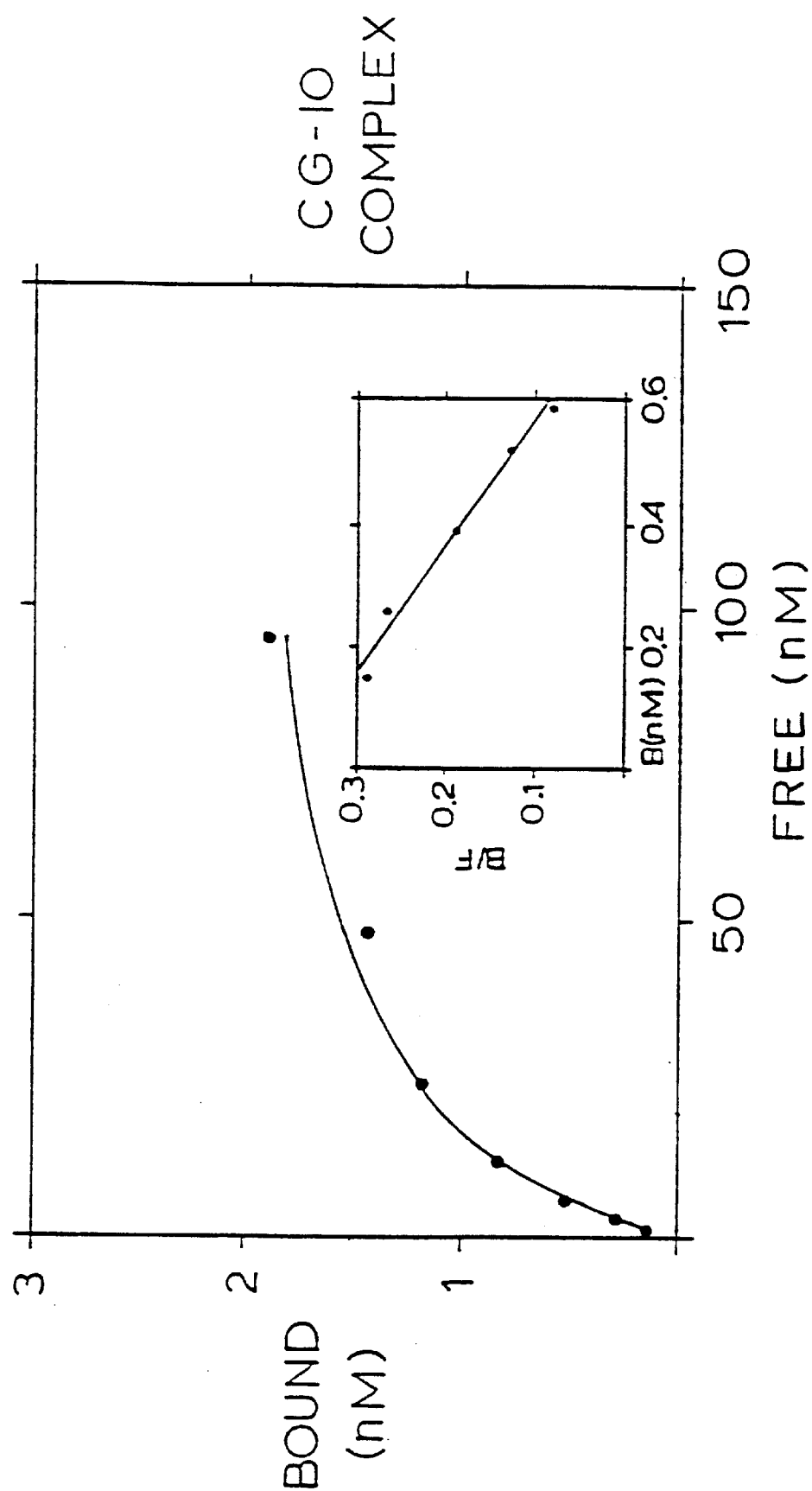

ANTIBODIES DIRECTED AGAINST BINDING-ASSOCIATED EPITOPES

RELATED APPLICATIONS

This is a division of application Ser. No. 09/235,592, filed Jan. 22, 1999, which is a continuation of application Ser. No. 08/464,726, filed Jul. 31, 1995, now U.S. Pat. No. 5,925, 741, issued Jul. 20, 1999, which is based upon PCT International Application No. PCT/US93/12639, filed Dec. 29, 1993, claiming priority of Israeli Application Nos. 104291 and 104767, filed Dec. 31, 1992 and Feb. 17, 1993, respectively.

FIELD OF THE INVENTION

The present invention concerns novel antigenic epitopes which become substantially more accessible after binding of two members of a binding couple, e.g. ligand-receptor binding, antibody-antigen binding, etc. These novel antigenic epitopes will be referred to herein at times as "binding associated epitopes (BAE). A specific aspect of the present invention concerns BAE which are revealed after virus-receptor interaction, e.g. HIV-CD4 interaction.

The present invention further concerns antibodies, particularly monoclonal antibodies, directed against BAEs, and further concerns the use of such antibodies or BAEs in diagnostics and treatment.

BACKGROUND OF THE INVENTION AND PRIOR ART

Binding of two members of a binding couple, e.g. a virus to its receptor on a cell membrane, is a complex interaction which may involve, inter alia, a conformational change in the receptor and likely also in the viral receptor-binding protein. The study of such conformational changes may have various important therapeutic implications.

A virus-receptor interaction which has been studied extensively in recent years is that of the HIV (Human Immunodeficiency Virus) to the CD4 protein which is expressed by and present on membranes of T lymphocytes, some macrophages and likely also on several other kinds of cells. An HIV protein, gp120, which has a binding affinity to the CD4 receptor was discovered, and the receptor recognition sites in this protein have been at least partially identified. Seeing that the binding between the HIV virus or its gp120 protein to the CD4 receptor and the occurrences following such interaction are critical phases in the infection process, it is believed that agents which will interfere with these infection stages will likely be useful as drugs in treating AIDS and particularly in inhibiting the progress of the HIV infection. It has been proposed to use antibodies which recognize either the CD4 receptor, the gp120 protein or the complex which is formed following binding, as it was believed that such antibodies may form useful agents in inhibiting the infection process. Monoclonal antibodies (mAbs) useful for this purpose have been proposed, amongst others, by Celada et al. 1990 (*J. Exp. Med.,* 172, 1143–1150), Celada, 1992 (WO 92/05799) and Healey et al., 1990 (*J. Exp. Med.,* 172, 1223–1242) These references disclosed antibodies directed against CD4 which were shown to prevent syncytium formation without interfering with the gp120/CD4 complex formation. However, all the antibodies described to date were not found to be useful in treatment since they either bind well to CD4 receptors and thus may interfere with the normal function of non-infected CD4 bearing cells or, where the antibodies were directed to an epitope in the virus and specifically in the gp120 protein, they were as a rule found to be strain and even isolate-specific.

OBJECTS OF THE INVENTION

It is an object of the present invention to provide antigenic epitopes associated with binding of two members of a binding couple to one another (BAE).

It is another object of the present invention to provide binding associated antibodies capable of binding to a complex consisting of two members of a binding couple, with a higher affinity than to each member by itself.

It is another object of the present invention to provide medicinal and diagnostic uses of such epitopes or antibodies.

The remaining objects of the present invention will be revealed in the following description and claims.

GENERAL DESCRIPTION OF THE INVENTION

The present invention is based on the surprising finding that upon binding of two members of a binding couple, certain novel antigenic epitopes are revealed or exposed and as a result become accessible to antibodies. When a complex of the two members is injected to an animal, an immune reaction is elicited and some of the produced antibodies are such which bind to the complex with a substantially higher affinity than to either of the two members individually.

Hybridomas producing such antibodies can be prepared and monoclonal antibodies produced by such hybridomas may be used for the isolation of the epitopes and for various diagnostic and therapeutic purposes.

The epitopes by themselves may be utilized for producing specific antibodies or in some cases for vaccination.

The novel epitopes of the invention may consist of an amino acid sequence present in one of the two members of the binding couple which becomes accessible to antibodies or resumes a new conformation after inding of the two members to one another; or may consist of a plurality of sequences either all in one member or being distributed between the two members but become associated with one another to form an antigenic epitope, after binding of the two members to one another.

The present invention thus provides, by one of its aspects, an antigenic epitope which is a member of a group consisting of:

(i) an epitope consisting of an amino acid sequence in a member of a binding couple, which becomes substantially more accessible to antibodies or resumes a new conformation after binding of the two members to one another.
(ii) an epitope consisting of two or more amino acid sequences in a member of a binding couple which upon binding of the two members, become closely associated to form an antigenic epitope, and
(iii) an epitope consisting of two or more amino acid sequences, at least one being in one member of a binding couple, and at least one other being in the other member of the binding couple and upon binding of the two members, said two or more amino acid sequences become closely associated with one another to form an antigenic epitope;

said antigenic epitope being immunogenic.

An epitope of the kind defined under (i) will be referred to herein at times as "linear revealed epitope"; an epitope of the kind defined under (ii) as a "discontinuous revealed epitope" and an epitope of the kind defined under (iii) will be referred to herein at times as "combination epitope".

The novel BAE may be an epitope which is revealed or exposed in an immunocomplexed antigen, i.e. in an antibody-antigen complex; after ligand-receptor bindings, e.g. hormone-receptor, neurotransmitter-receptor, toxin-receptor, virus-receptor bindings; etc. A specific embodiment of the present invention concerns an epitope which is revealed after binding of a virus to its receptor, in particular epitopes which are revealed or exposed after binding of HIV through its gp120 protein to a soluble or membrane associated CD4 receptor protein. Another embodiment concerns an immunocomplexed gp120 epitope, i.e. an epitope which is revealed or exposed after binding of gp120 to an antibody against it produced in the body during an immune reaction following an HIV infection.

The present invention further provides, by another of its aspects, antibodies which bind to a complex consisting of two members of a binding couple with a substantially higher affinity than with each of the two members by themselves. A specific embodiment of this aspect of the invention concerns antibodies which bind to a complex formed between the HIV gp120 protein and the CD4 protein and such which bind to an immunocomplexed gp120 with a substantially higher affinity than to either of the members of the complex by themselves.

A higher affinity of binding may be 5 fold, preferably 10 fold higher affinity of binding to the complex as compared to binding affinity of the antibody to each of the members of the complex by themselves, as tested by at least one standard assay such as ELISA, RIA (Radioimmunoassay), or by means of a FACS (Fluorescent Activated Cell Sorter) analysis. It should be noted that at times higher affinity of binding may be seen by such standard procedures, but may not be seen to the same extent in other experimental procedures. For example, a cryptic BAE normally effectively revealed after complex formation may also be exposed in a protein without complex formation when, for example, denatured on a SDS gel. In case the test is performed on proteins on an SDS gel, a higher affinity of binding to the complex may not be seen, although present in the non-denatured proteins.

The antibodies of the invention may be poly- or monoclonal, although for reasons of highly specificity and ease of obtaining relatively large quantities, monoclonal antibodies are generally preferred.

The epitopes of the invention may be detected and isolated by various methods, some of which will be briefly detailed herein:

1. Western blotting analysis: CD4 or gp120 are digested by a number of proteolytic enzymes. The resulting proteolized fragments are gel electrophoresed on SDS acrylamide gels, and blots are prepared by transferring the separated fragments from the gel to a suitable filter. The filter is then probed with a series of labelled mAbs. A fragment that repeatedly binds to a mAb of interest is transfered to a PVDF (poly venil difluoride—Millipore Inc. Ma.) membrane and is then sequenced by any of a number of sequencing methods known per se.
2. Pepscan analysis: (see Geysen et al., 1984. Proc. Natl. Acad. Sci. U.S.A., 81: 3998–4002; Geysen et al., 1985. Proc. Natl. Acad. Sci., U.S.A.., 82: 178–182). A series of synthetic peptides corresponding to the complete sequence of the CD4 or gp120 molecules are produced in multiwell ELISA plates by solid phase Merrifield peptide synthesis. The synthetic peptides are then screened by incubating the plates with labelled mAbs of interest. An antibody that binds to a specific peptide is therefore mapped to that corresponding sequence.

This method is suitable for linear revealed epitopes and is obviously not suitable for mapping discontinuous epitopes or combination epitopes. In order to identify discontinuous or combination epitopes, the following method may be used.
3. Epitope Libraries: (see Scott et. al., 1990., Science 249: 386–390; Delvin et al., 1990., Science 249: 404–406; Cwirla et al., 1990., Proc. Natl. Acad. Sci. U.S.A. 87: 6378–6382). A library consisting of a collection of the entire repertoire of combinations of peptide sequences presented on the surface of filamentous phages is constructed. (Thus, for example, the complete collection of hexapeptides is $20°=6.4\times10^7$ peptides). The phage containing an epitope of interest is then enriched by a Biopanning method in which a few microliters containing the entire library are first incubated with a suitable mAb in a flask. The library-mAb mixture is then transferred to a petri dish containing immobilized streptavidin. Only phages bound by the biotinylated mAb will bind to the streptavidin in the dish and after washing away of the non-bound phages, the bound phage is grown in the plate and ultimately sequenced to reveal the desired epitope.

The method under 3 is particularly suitable for the detection of discontinuous epitopes or combination epitopes, due to the existence, in such libraries, of "mimetopes", i.e. linear peptides that functionally mimic such which can naturally be produced by discontinuous distant residues.

In order to prepare the antibodies of the present invention laboratory animals are injected with complexes formed between the two members of a binding couple such as complexes formed between viruses or viral particles and the receptor to which they bind, e.g. gp120/CD4 complexes in the case of the HIV or with immunocomplexed viruses or viral particles, e.g. immunocomplexed gp120. Following injection and the development of an imune reaction, spleen cells may be isolated from these laboratory animals and hybridomas may then be prepared by methods generally known per se. The hybridomas are then screened for such which secrete antibodies which react with the complex with higher affinity than with each of the individual components.

Hybridomas producing monoclonal antibodies of the invention constitute another aspect of the present invention. One hybridoma cell line designated hereinbelow as CG-10 was deposited on Feb. 4, 1993, at the European Collection of Animal Cell Culture (ECACC), Porton Down, Salisbury, Wiltshire, SP4 OJG, United Kingdom, and was assigned the Accession No. 93020415.

The antibodies of the invention can be used as a therapeutic agent for a variety of applications such as for the treatment of viral infections in order to inhibit further propagation of the infection. For example, antibodies which are specific for gp120/CD4 complexes may have an important potential use in the treatment of AIDS. As known, for human medicinal use, the mAbs should preferably be "humanized", e.g. by methods known per se such as CDR loop grafting (see Verhoyen et al., 1988, *Science* 239: 1534–1536). Alternatively, the mAbs should be of human origin, i.e. human mAbs. Additionally, antibodies of the invention may have various diagnostic applications, e.g. anti-immunocomplexed gp120 be used for diagnosis or staging of HIV infections.

The epitope of the invention may have various uses such as in diagnostics, as well as in immunization. For similar uses also anti-idiotype antibodies against the above antibodies of the invention may be used. Such anti-idiotype antibodies also constitute an aspect of the invention.

In the following description specific reference will at times be made to HIV-related epitopes which become accessible to antibodies upon binding of HIV or its gp120 protein to the CD4 protein and to an anti-immunocomplexed gp120 antibody and to antibodies which specifically bind to complexes formed between gp120 and CD4 proteins or bind to immunocomplexed gp120. It will no doubt be appreciated by the artisan that although these embodiments of the present invention are preferred embodiments, the invention is not limited thereto.

Antibodies available to date which were proposed for use in AIDS treatment were unsuitable for this purpose. On the one hand, prior art antibodies directed against different epitopes of gp120, were found to be ineffective in inhibiting viral infections particularly in view of the very high strain and isolate variability of this protein. On the other hand, prior art antibodies directed against the CD4 protein might interfere with the normal functions of non-infected CD4-expressing cells. Against this, the antibodies of the present invention do not possess these drawbacks associated with prior art antibodies. The antibodies of the invention, in the specific case of HIV, are specifically directed to epitopes which are revealed or become more accessible after interaction between the HIV and the CD4 protein, and will thus inhibit progress of the infection, e.g. the formation of syncytia of lymphocytes, without interferring with the normal functions of non-infected CD4-expressing cells. Furthermore, such antibodies are also not likely to be strain or isolate specific, since even if the epitope is of a viral origin, the fact that it is not accessible prior to binding means that it is not subject to selective forces as in the case of normally exposed epitopes. In addition, if the antibodies are of a suitable kind, their binding to the complex may also elicit a cellular cytotoxic immune response against the infected cells.

The antibodies of the present invention may be conjugated to radioactive or cytotoxic substances. Such conjugated antibodies will localize only on infected cells and will thus serve as specific targeted chemotherapeutic agents and will destroy only infected cells without severely damaging normal, non-infected cells of the same kind.

Furthermore, anti immunocomplexed gp120 mAbs may serve in the diagnosis of HIV infections. To enable their use in detection in a diagnostic procedure, such antibodies may preferably be conjugated to various markers, such as radioactive or fluorescent substances, or enzymes such as horseradish peroxidase etc.

By another aspect of the present invention, there is provided a pharmaceutical composition for treating a viral infection comprising, as an active agent, an antibody according to the invention.

By another aspect of the invention there is provided an antiviral vaccine comprising as an active agent, an epitope of the invention.

By another aspect, the present invention provides a method for treating a viral infection, comprising administering to a patient an effective amount of an antibody according to the invention.

By another aspect, the present invention provides a method for the diagnosis or staging of a viral infection, utilizing the antibodies of the invention. By one embodiment the method comprises contacting cells susceptible of being infected by the virus with an antibody of the invention, and then detecting the presence of such antibodies on the cells' surface. By another embodiment, the method comprises contacting a body fluid sample with an antibody against an immunocomplexed virus or viral particle or with such an antibody conjugated with a detectable marker and then detecting the formation of immunocomplexes with said antibody or conjugate. Where the antibodies of the present invention are not conjugated to a detectable marker, a second antibody directed against the antibodies of the invention, conjugated to a detectable marker will typically be introduced for the assay.

By another aspect of the invention there is provided a method for immunizing an animal against a viral infection comprising administering to a subject an effective amount of a BAE epitope of the invention, of a kind which is revealed after binding of a virus to its receptor.

The invention will now be described with reference to specific embodiments described in the following examples, with reference at times to the Figures in the annexed drawings.

EXAMPLES

Example 1

Production of CD4/gp120 Complexes

Figures 1, 1A:
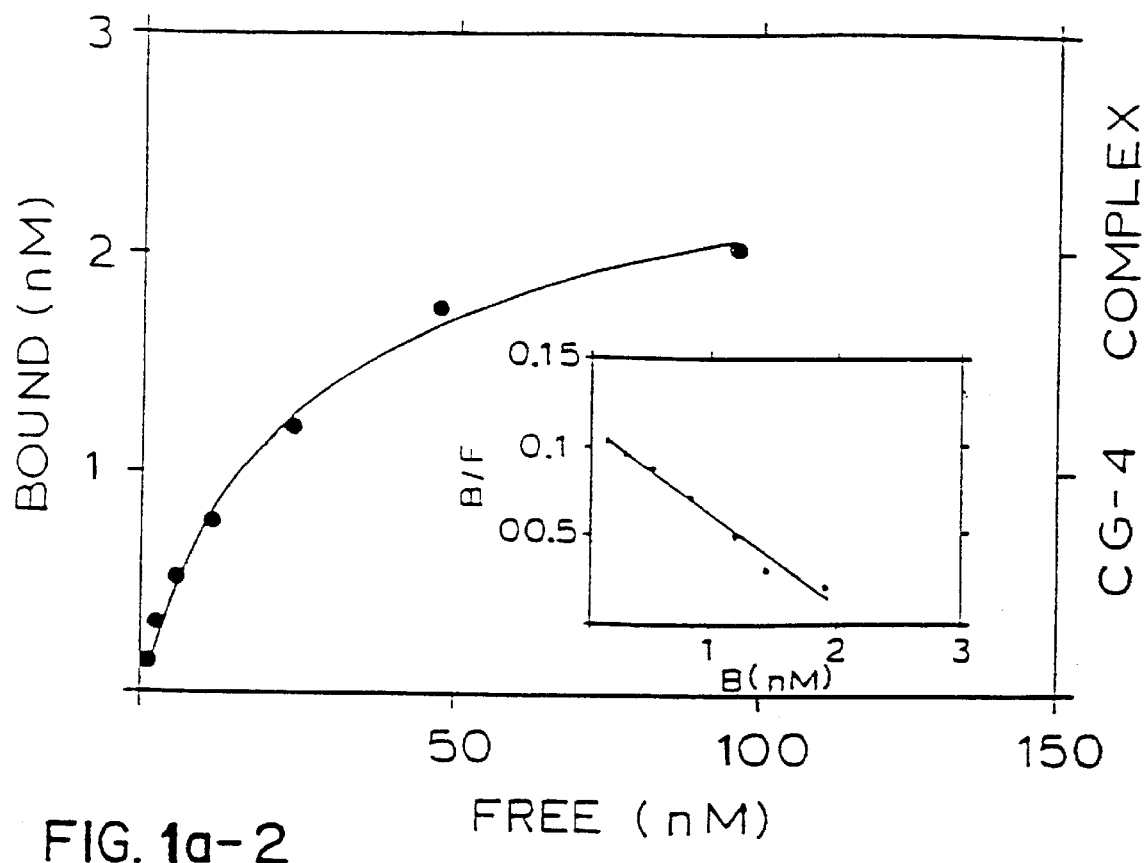
FIG. 1 shows a series of scatchard plots obtained with five different antibodies reacted with either the complex formed between gp120 and CD4 or with either of these two agents by themselves: a) antibody CG-4; b) antibody CG-9; c) antibody CG-10; d) antibody CG-25; and e) antibody CG-76.

Recombinant gp120 produced in a baculavirus expression system was obtained from American Bio-Technologies. Recombinant soluble CD4, produced in Chinese hamster ovary (CHO) cells, was obtained from DuPont. CD4/gp120 complexes were prepared by a number of procedures. For example, 100 $\mu$g of gp120 can be mixed with 50 $\mu$g of CD4 in Tris buffered saline (TBS) at 4° C. for 12 hours. The complex is then dialysed against the same buffer prior to injection.

In order to verify that a CD4/gp120 complex was formed, ELISA assays were used. In this assay, either gp120 or CD4 were immobilized on a plate and then a soluble counterpart (CD4 or gp120, respectively) was added to the plate. Subsequently, the plates were probed with a first antibody being either anti-gp120 (obtained from American Bio-Technologies) or OKT4 and OKT4A (which are anti-CD4 antibodies obtained from Orthodiagnostics Inc.) followed by a second alkaline phosphatase conjugated anti-mouse antibody.

For the ELISA assay Costar EIA/RIA 96 well plates (N3590) were coated with 50 $\mu$l of various concentrations of gp120 or CD4 in TBS (tris-buffered saline) overnight at 4° C. The plates were then washed in TBS and blocked with 3% BSA in TBS for 1 hour at room temperature (RT). Then 50 $\mu$l of 5 $\mu$g/ml solution of either recombinant CD4 or recombinant gp120 was added into the wells. The wells were rinsed and the appropriate mAb in 0.3% BSA/TBS was added to them and incubated at RT for 2–3 hours. The wells were then washed with TBS and the second antibody (alkaline phosphatase conjugated goat anti-mouse antibody

[Sigma, A-0162]) was added (1:1000 in 0.3% BSA/TBS) and incubated for 1 hour at RT. After washing the wells, they were reacted with p-nitrophenyl phosphate (1 mg/ml in 1M diethanolamine buffer pH 9.8/0.5 mM $MgCl_2$) and read at 405 nm.

Exemplary results of such a complex analysis is shown in the following Table I (the numbers in the Table represent $OD \times 10^{-3}$):

TABLE I

| Plated gp120 µg/ml | OKT4A* | OKT4 | Plated CD4 µg/ml | OKT4A | OKT4 |
|---|---|---|---|---|---|
| 10.0 | 27 | 640 | 5.0 | 206 | 729 |
| 5.0 | 23 | 773 | 2.5 | 135 | 492 |
| 2.5 | 27 | 313 | 1.25 | 42 | 291 |
| 1.25 | 29 | 116 | 0.60 | 22 | 138 |

*OKT4A - an anti-CD4 antibody which recognizes only the CD4 protein which is not bound to gp120 (see: Sweet et al. (1991) Current Opinion in Biotechnology 2: 622–633).

Example 2

Production of Anti-Complex mAbs 3 mice were immunized with a CD4/gp120 complex that had been extensively dialyzed. A total volume of 1 ml complex prepared as in Example 1, was dialyzed against 2 liters of Tris buffered saline (TBS), (total volume 6 liters) for 12–14 hours at 4° C. These mice developed a good immune response against both CD4 and gp120.

A plurality of hybridoma cell lines were prepared from these mice. From the spleen of one of the injected mice, which was found to be extremely large, about $4 \times 10^5$ cells were obtained and 4 aliquots of about $10^5$ cells were taken separately. Each aliquot was fused with NS-1 cells. Two fusions were processed in parallel. A total of 1170 clones were obtained and after 10 days of culture, the media were screened for antibodies directed against CD4/gp120 complex in an ELISA essay which was similar to that described above in Example 1 with a difference in that a CD4/gp120 complex was immobilized on the plates (5 µg gp120: 2.5 µg CD4/ml).

147 clones were found positive and these were then rescreened with immobilized CD4/gp120 complex as well as separate immobilized CD4 and gp120 in a similar ELISA assay to the above. Of the original clones only 81 continued to secrete antibodies and of these 15 were selected for future characterization. Out of these, 13 clones were found to be stable and were injected into mice for a successful production of ascites fluids.

Ascites fluids of all 13 mAbs described were produced, lyophilized and analyzed for their ability to bind CD4, gp120 and CD4/gp120 complexes. The mAbs were tested by ELISA assays, FACS analysis and Western Blots. A collection of 10 mAbs was identified as being interesting for further analysis and the result of their binding studies is shown in the following Table II.

TABLE II

| | mAb | subclass | gp120/CD4 | gp120 | CD4 |
|---|---|---|---|---|---|
| 1 | CG-1 | IgG1 | +++ | – | +/– |
| 2 | CG-4 | IgG1 | +++ | +++ | – |
| 3 | CG-7 | IgG1 | +++ | – | +/– |
| 4 | CG-8 | IgG1 | +++ | – | +/– |
| 5 | CG-9 | IgG1 | +++ | – | ++ |
| 6 | CG-10 | IgG1 | +++ | – | – |
| 7 | CG-25 | IgG1 | +++ | – | ++ |
| 8 | CG-30 | IgG1 | +++ | – | ++ |
| 9 | CG-40 | IgG1 | +++ | +++ | – |
| 10 | CG-76 | IgG1 | +++ | – | +++ |

In the above table, +++ shows a strong reaction wheras a – shows no reaction.

Of these antibodies, several including those designated CG-1, CG-7, CG-8, CG-9, CG-10, CG-25 and CG-30, are such having the characteristics of the antibodies of the present invention. Of those antibodies, CG-10, as can be seen from the above results, is specific only for the CD4/gp120 complex.

Example 3

Scatchard Analysis of Five mAbs

A series of scatchard analyses were performed in order to determine the binding affinity of five mAbs (CG-4, CG-9, CG-10, CG-25 and CG-76) for the CD4/gp120 complexes as compared to their binding affinity for isolated CD4 or gp120.

Figures 1, 1A, 2:
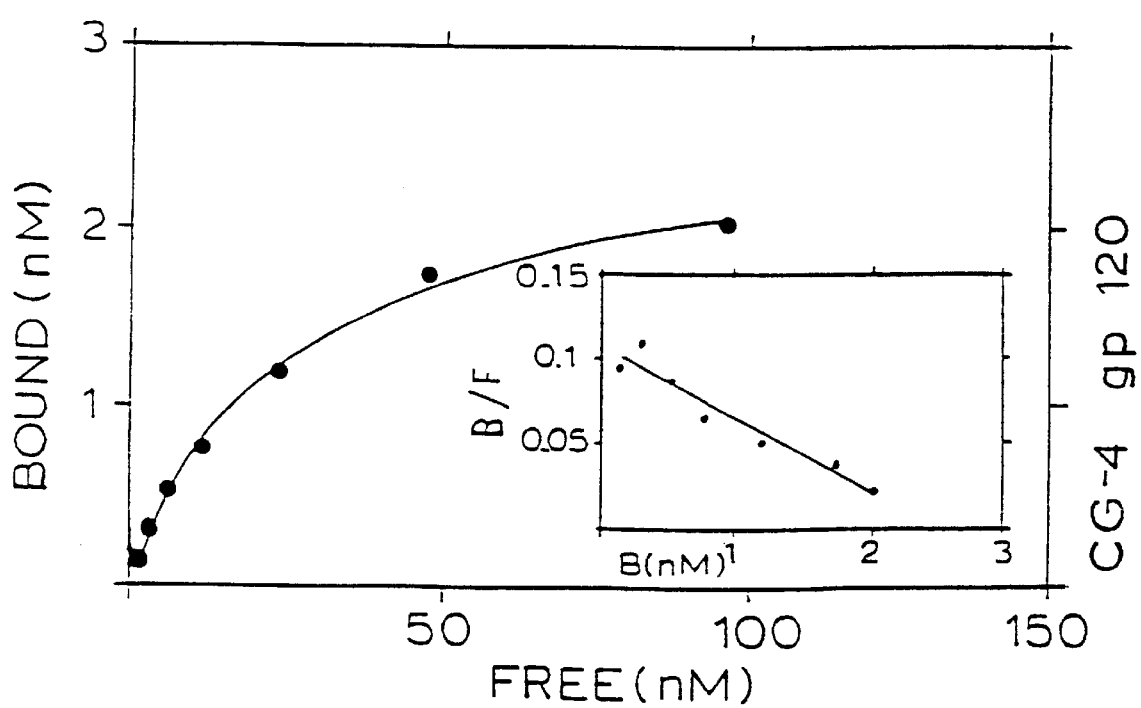
FIG. 2 shows the affinity of binding of four of the antibodies to either the complex or to CD4.
Figures 1, 1B:
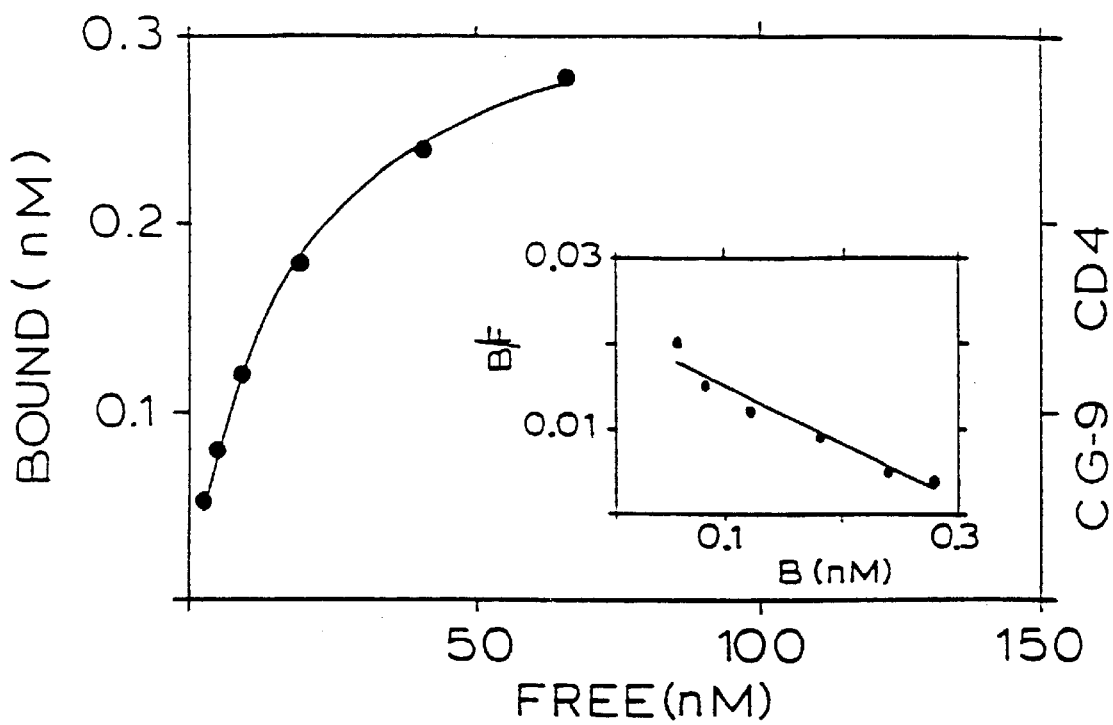
Figures 1, 1B, 2:
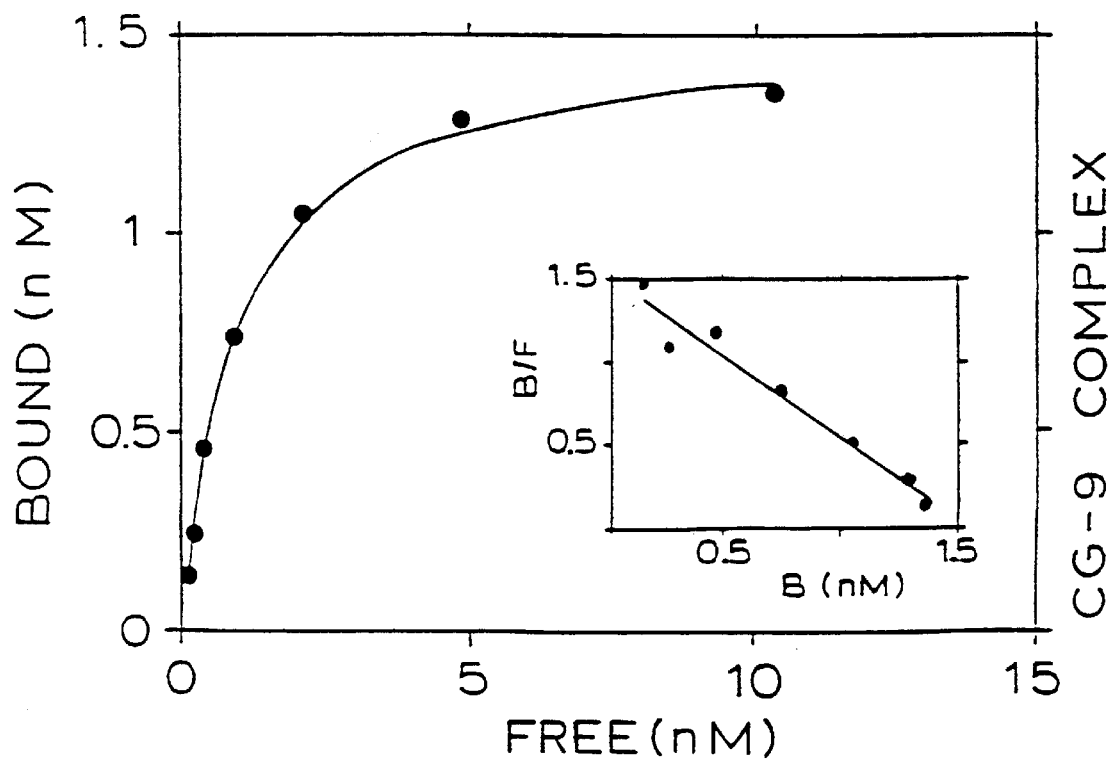
Figures 1, 1D:
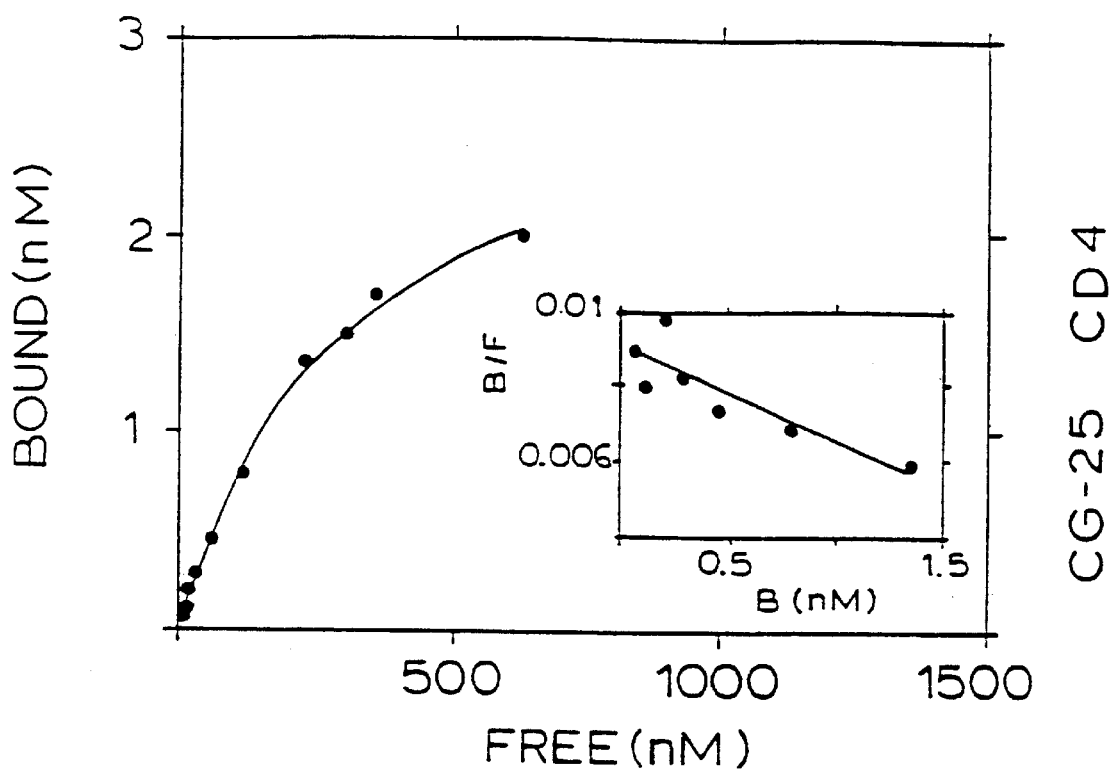
Figures 1, 1D, 2:
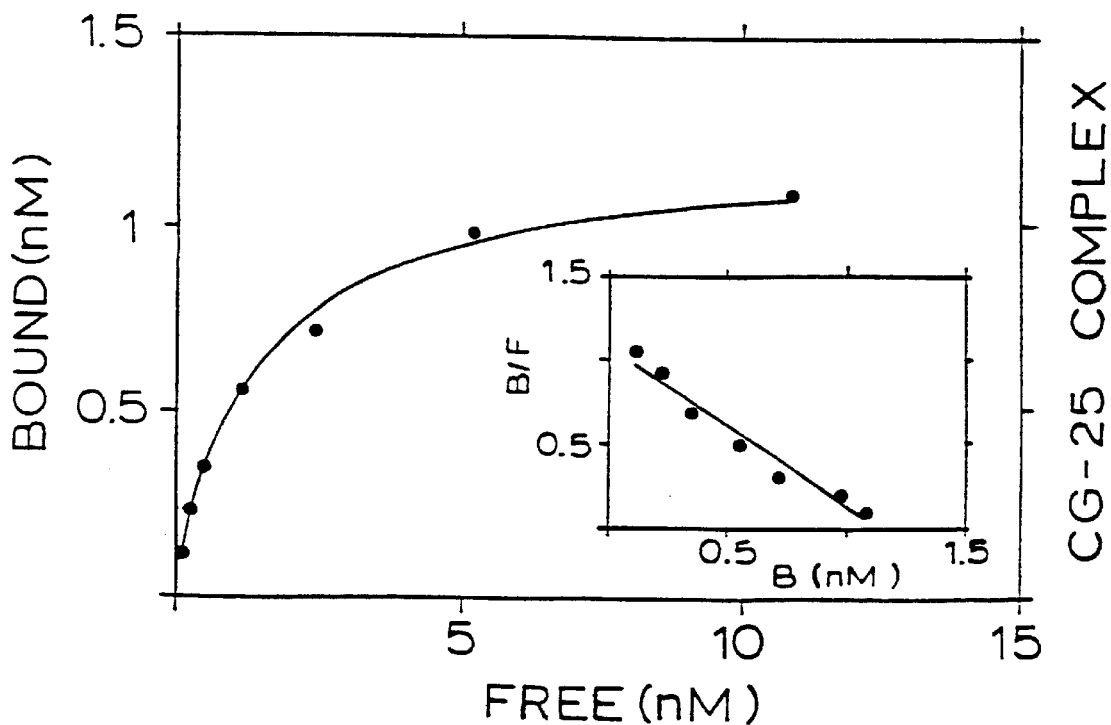
Figures 1, 1E:
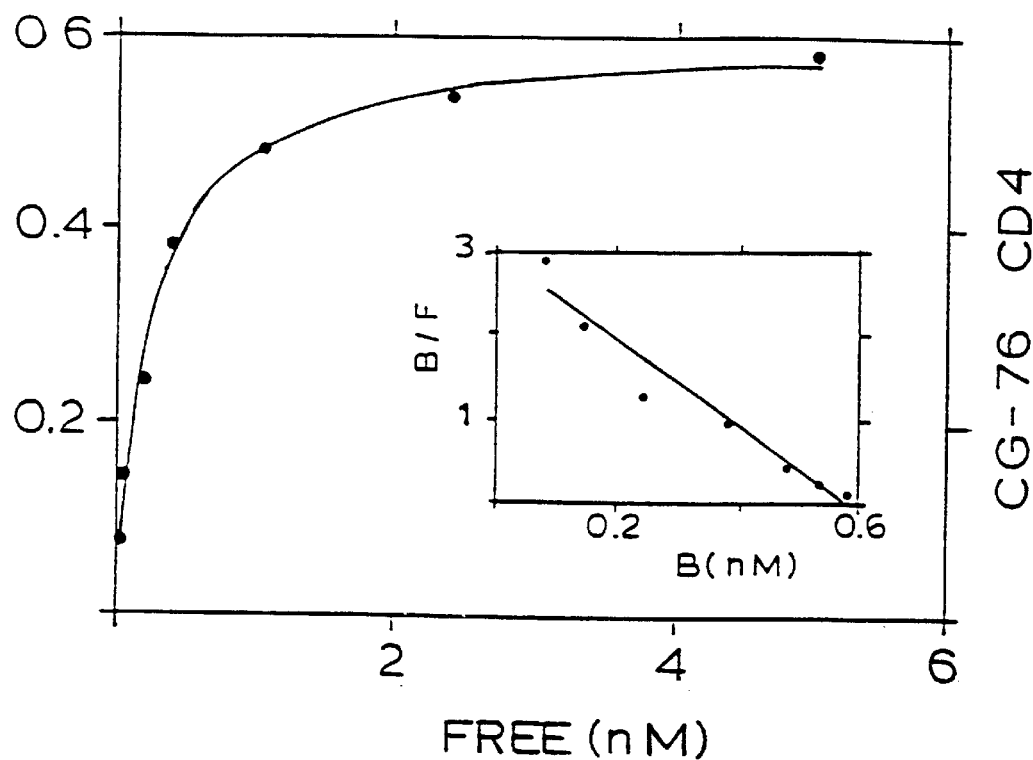
Figures 1, 1E, 2:
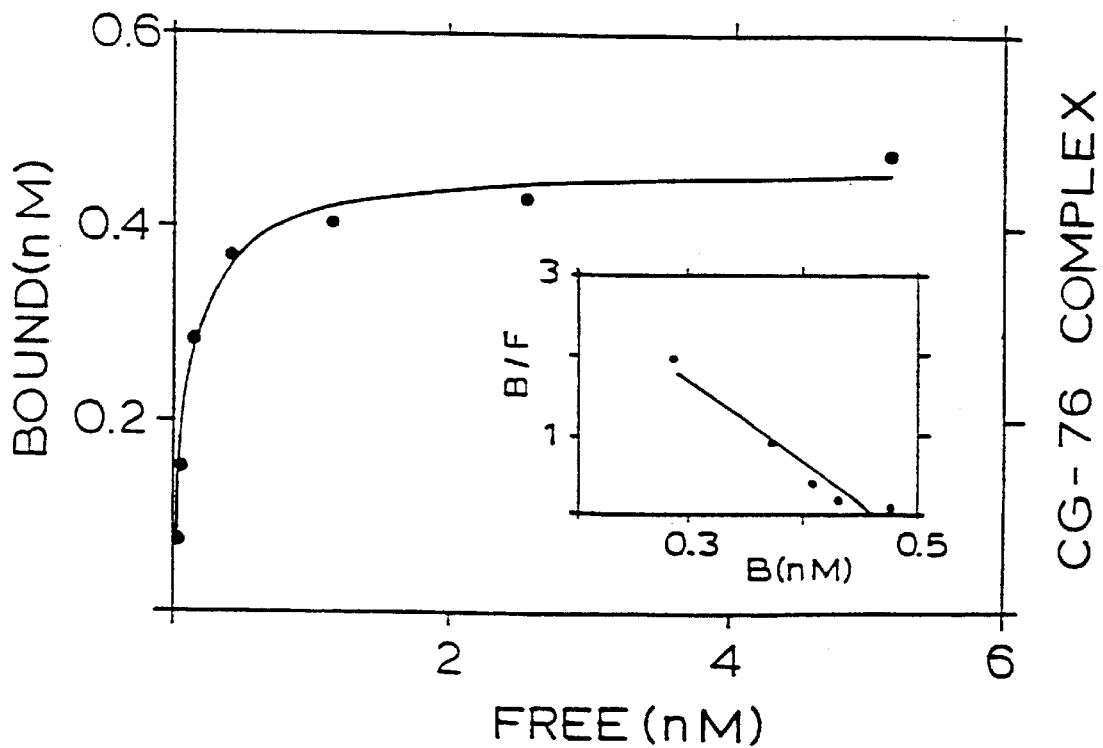
Figure 2:
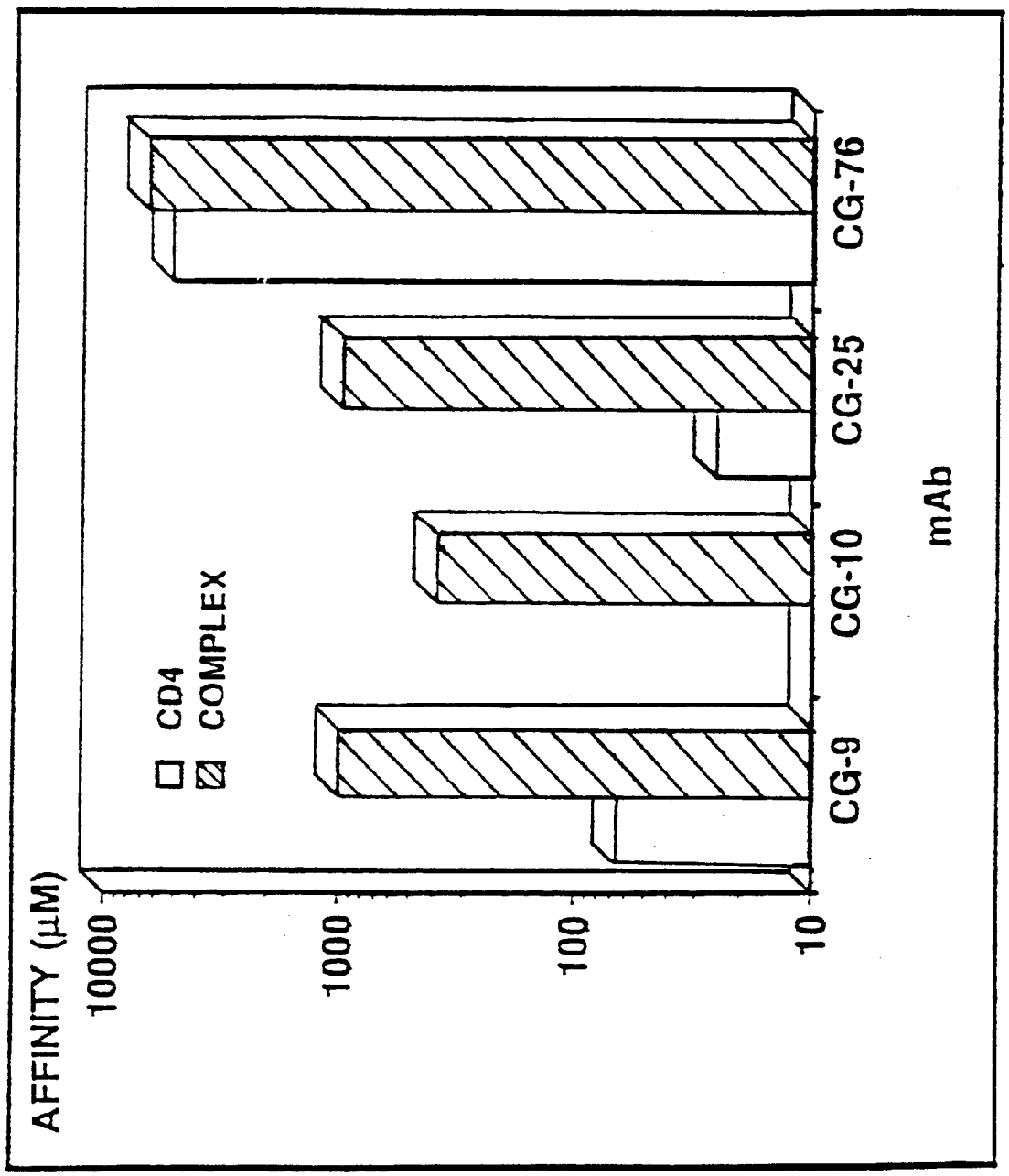
Figure 3A:
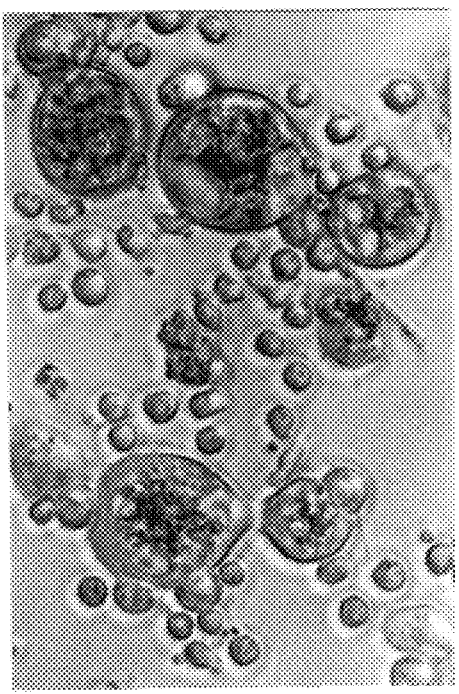
FIG. 3 is a micrograph showing syncytium formation between CD4 expressing CEM cells and gp120 expressing BSC1 cells without antibodies (A) or in the presence of the various monoclonal antibodies (B–I).
Figure 3B:
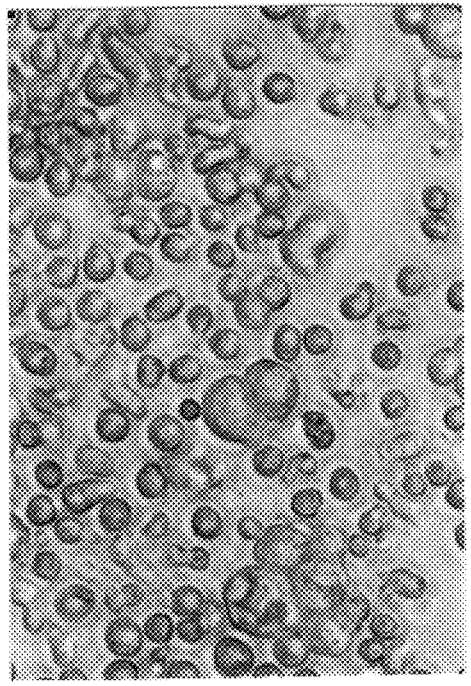
Figure 3C:
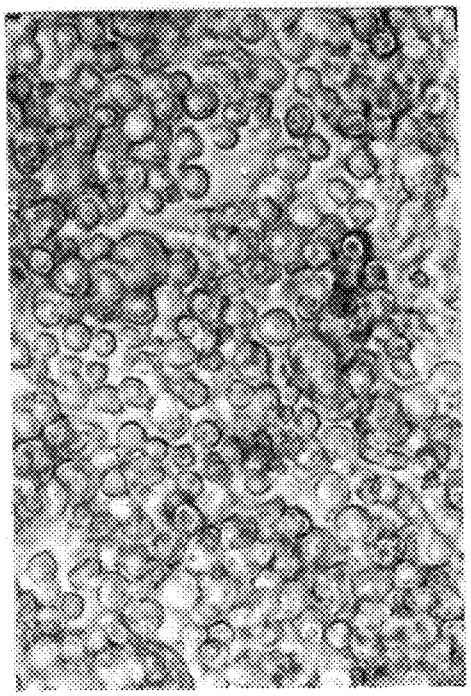
Figure 3D:
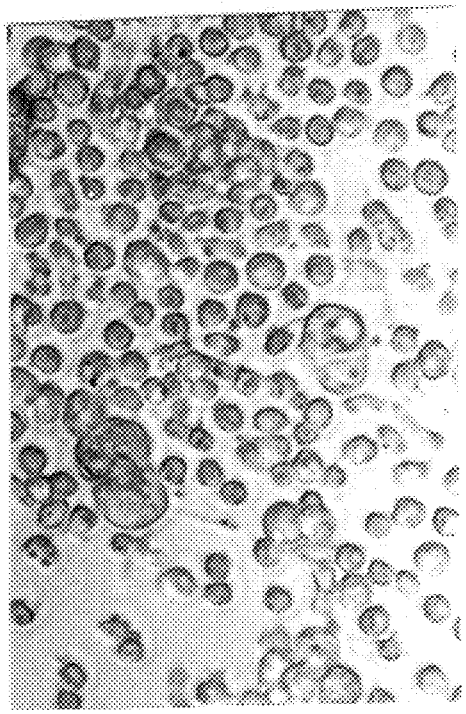
Figure 3E:
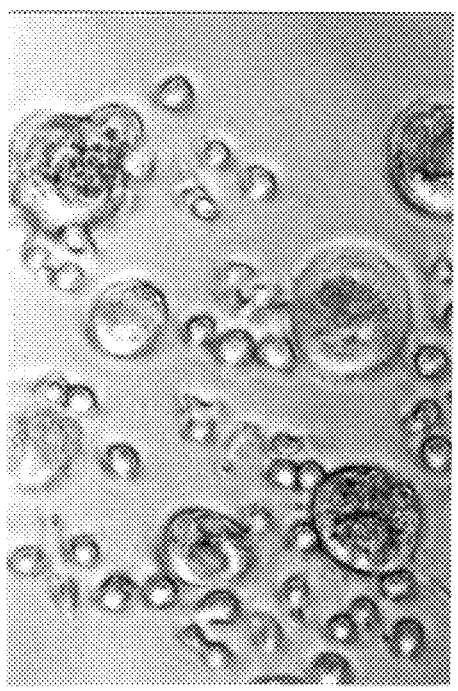
Figure 3F:
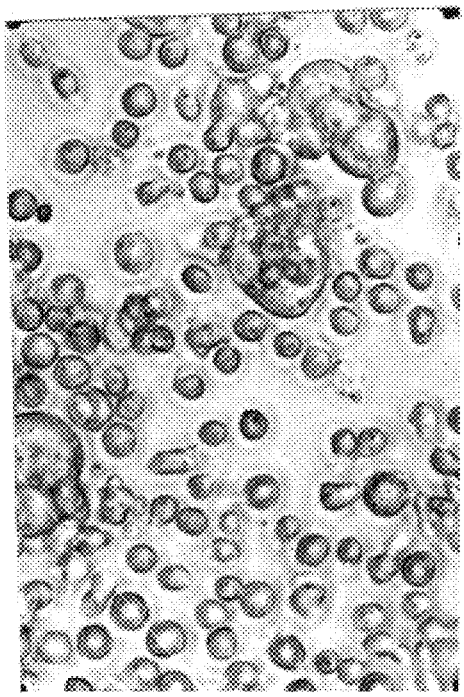
Figure 3G:
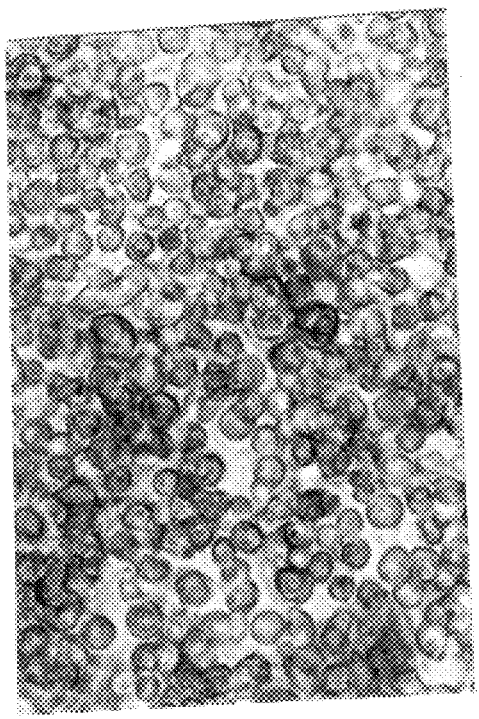
Figure 3H:
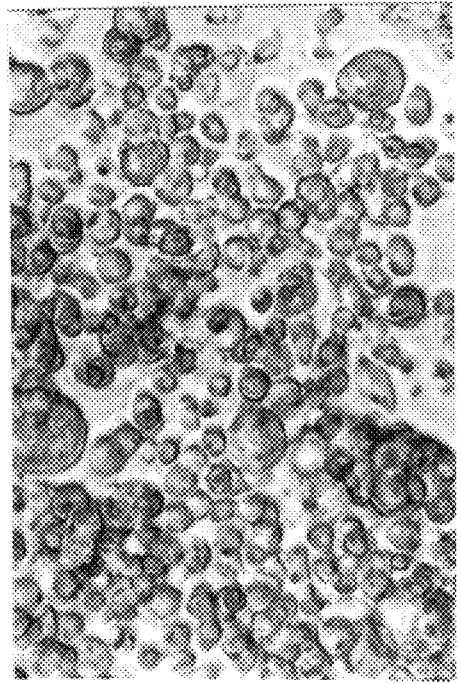
Figure 31:
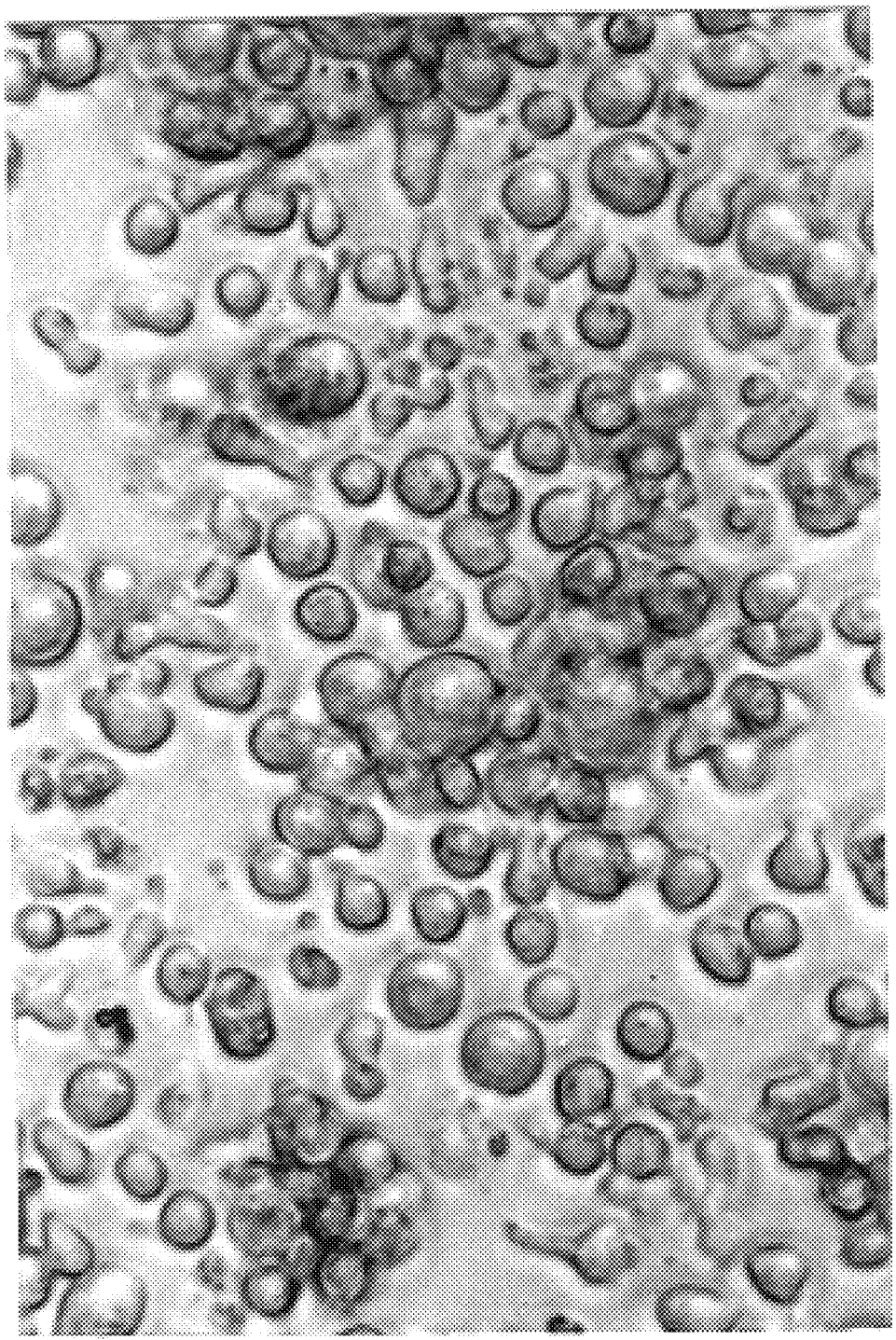

CD4, gp120 and CD4/gp120 complexes were immobilized in wells of ELISA plates. The tested mAbs were iodinated with $^{125}I$ and the immobilized antigens were incubated with the iodinated mabs. The scatchard plots of the five above mentioned mAbs are seen in FIG. 1. The affinity of binding of four of the mAbs to either the complex or to the CD4 is shown in FIG. 2.

mAbs, CG4 and CG-76 showed similar binding affinities to isolated CD4 and CD4/gp120 complexes and may therefore be of the type previously reported by Celada et al.

As opposed to this, mAbs CG-9 and CG-25 showed a respective 10 and 100 fold higher binding affinity to the CD4/gp120 complex, as compared to their binding affinity to CD4 alone. Furthermore, mAb CG-10 had no affinity for the isolated CD4 and bound exclusively to the CD4/gp120 complex.

Example 4

Inhibition of Syncytium Formation

The formation of syncytia between vaccinia BSC1 cells (African green monkey kidney cells) infected with the recombinant vaccinia clone VEP16 (see Ashorn et al., 1990 J. Virol. 64 2149–2156) expressing gp120 on their surface and CEM cells (a human T helper lymphocyte cell line) expressing CD4 on their surface was tested. Generally, BSC1 cultures were infected with recombinant vaccinia (5 pfu/ml) expressing cell surface gp120. These cells were then mixed with CEM cells in the presence of varying amounts of mAbs and incubated for different periods of time. The degree of syncytia formation was monitored and thus the extent of neutralization potential for the various mAbs was estimated.

As is shown in panel A of FIG. 3, when infected BSC1 cells were mixed with CEM cells, syncytia were formed within a few hours. The potential of the different antibodies to neutralize syncytium formation was tested by pre-incubation of CEM cells for 5 to 12 hours with the tested mAbs before the addition of the infected BSC1 cells (panels C, G, H and I) or by the addition of the tested mAbs simultaneously with the BSC1 cells (panels B, D, E and F).

The results are shown for the following mAbs which were added in the indicated amounts:

Panel B: 10 μg of mAb CG-9; Panel C: 1μ of mAb, CG-25; Panel D & G: 1 μg of CG-76; Panel H: 1μ of mAb CG-10; and Panel I: 1 μg of CG-76.

As seen in FIG. 3, all the tested mAbs (CG-9, CG-10, CG-25 and CG-76) showed at least some syncytium neutralizing activity, each to a different extent. In addition, the pre-incubation of the mAbs with CD4 expressing CEM cells improved the neutralizing activity of the mAbs.

Example 5

Preliminary Analysis of Sera Obtained from HIV+ Hemophilia Patients

Sera from five HIV+ hemophilia patients were tested for their potential to inhibit the binding of several mAbs to CD4/gp120 complexes in a competitive ELISA.

For the competitive ELISA assay Costar EIA/RIA 96 well plates (N3590) were coated with 50 μl of 5 μg/ml CD4/gp120 complex in TBS (tris-buffered saline) overnight at 4° C. The plates were then washed in TBS and blocked with 3% BSA in TBS for 1 hour at room temperature (RT). Then, the wells were rinsed and 50 μl of the appropriately diluted mAb in 0.3% BSA/TBS was added to them with 50 μl of TBS (control wells) or 50 μl of the mAb and 50 μl of the tested serum were added simultaneously (test wells) and incubated at RT for 2–3 hours. The wells were then washed with TBS and the second antibody (alkaline phosphatase conjugated goat anti-mouse antibody [Sigma, A-0162]) was added (1:1000 in 0.3% BSA/TBS) and incubated for 1 hour at RT. After washing the wells, they were reacted with p-nitrophenyl phosphate (1 mg/ml in 1M diethanolamine buffer pH 9.8/0.5 mM $MgCl_2$) and read at 405 nm.

The results of the competitive ELISA are shown in Table 3.

TABLE III

| #mAb | Pat. #1 | Pat. #5 | Pat. #8 | Pat. #9 | Pat. #11 |
|---|---|---|---|---|---|
| CG-1 | 50 | 40 | 55 | 70 | 0 |
| CG-4 | 78 | 87 | 68 | 75 | 60 |
| CG-7 | 59 | 61 | 68 | 70 | 0 |
| CG-8 | 43 | 60 | 58 | 71 | 0 |
| CG-9 | 11 | 38 | 20 | 27 | 0 |
| CG-10 | 65 | 87 | 98 | 91 | 68 |
| CG-25 | 25 | 44 | 22 | 41 | 0 |
| CG-30 | 0 | 40 | 0 | 21 | 0 |
| CG-40 | 16 | 44 | 0 | 8 | 0 |

The numbers (N) in the above table represent the % of inhibition calculated as follows:

$$N = \left[1 - \frac{\text{O.D. of binding of mAbx to CD4/gp120 in the presence of the tested serum}}{\text{O.D. of binding of mAbx to CD4/gp120}}\right] \times 100$$

Thus, for example, serum from patient no. 11 inhibited 68% of the binding of mAb CG-10 to immobilized complex.

The results in Table III show that sera from all five tested hemophilia patients can compete with the binding of mAb-CG-10 to the CD4/gp120 complex. It appears, therefore, that HIV infected hemophiliacs contain complex specific antibodies and that mAbs of the present invention may thus serve in the diagnosis of HIV infections.

Example 6

Detecting the Presence of gp120 in a Blood Sample Using the CG-10 mAb

The close proximity assay is a method for measuring the existence of receptor/ligand binding without the need to separate bound from free ligand (Hart, H. E. and Greenwald, E. B. *Mol Immunol.* 16, 265–267 (1979); Udenfriend. S. et al. *PNAS* 82, 8672–8676 (1982); Udenfriend S. et al. *Anal Biochem.* 161, 494–500 (1987); U.S. Pat. No. 4,568,649). This assay makes use of beads that have been impregnated with a scintillating dye having a desired receptor immobilized on their surface. The beads are mixed with a radioactive ligand and while the radiation emitted by non-bound ligand molecules in solution is quenched by the medium, the emission of a ligand which is bound by the receptor coating the scintillating beads, due to the close physical proximity, can interact with the dye and elicit a secondary photon. This scintillation is easily monitored and quantitated in a standard scintillation counter (in the absence of any additional scintillating fluid).

CD4 is immobilized on the surface of commercially available scintillating beads (Amersham product #RPN 141) using a commercially available mAb such as OKT4 or other mAbs such as CG-76 (see Example 2).

Alternatively, beads impregnated with a fluorophor (obtained from Nuclear Enterprises, Scotland, product #NE-102A) are directly coated with CD4 as follows: methyl groups are oxidized to COOH groups either with dilute nitric acid or with $KMnO_4$ and these are used to couple the CD4 via the water soluble carbodiimide reaction. The beads are washed to separate excess carbodiimide and unreacted CD4.

A tested blood sample is solubilized with Triton-X-100 and cleared from erythrocytes by methods known per se. The beads coated with CD4 are then mixed with the blood sample and a radioactive labeled CG-10 mAb (or any other mAb directed against the CD4/gp120 complex) is added to the mixture. The sample is read in a standard scintillation counter; a high reading indicating the presence of gp120 in the tested blood sample.

Another application in which CG-10 could be used as a diagnostic could employ such methods as Immuno-PCR in which the DNA template would be conjugated to CG-10 immunoglobulin. This could be done with the glycomoiety of the antibody.

Example 7

Production of Anti gp120/V3 Loop Complex mAbs

A gp120/anti-HIV-1V3 loop complex was prepared by mixing a mAb directed against anti-HIV-1 V3 loop$_{IIIB}$ designated M77 (obtained from Advanced Bioscience Laboratories, Inc., MD USA-ABL) with recombinant HIV-1 gp120$_{IIIB}$ (obtained from American Bio-Technologies-ABT). BALB/c mice were immunized with the prepared complex and hybridoma cell lines were prepared from the injected mice. Media from several clones obtained from these hybridomas were screened for antibodies directed against the gp120/anti V3 loop complex in an ELISA assay as described in Example 2. The clones that were found positive were retested for their affinity for the above complex as well as for separate gp120 and M77 mAb. mAbs that bound gp120$_{IIIB}$ were also tested for their affinity of binding HIV-2$_{ST}$ (a preparation of recombinant gp120 derived from an HIV-2$_{ST}$ isolate, purchased from SmithKline Beecham, King of Prussia, Pa.). The results of the binding studies of several of the mAbs is shown in the following table 4.

TABLE IV

| Clone | Type  | Complex | M77   | 120$_{IIIB}$ | 120$_{ST}$ |
|-------|-------|---------|-------|--------------|------------|
| 3F    | lgG1  | 1.204   | 0.035 | 0.193        | —          |
| 4D    | lgG1  | 1.093   | 0.044 | 1.090        | 0.629      |
| 4G    | lgG2b | 0.840   | 0.033 | 0.907        | 0.686      |
| 4H    | lgG1  | 1.063   | 0.083 | 0.379        | 0.564      |
| 7A    | lgM   | 0.884   | 0.045 | 0.944        | 1.238      |
| 7F    | lgG2a | 1.136   | 0.092 | 0.214        | —          |
| 8G    | lgG1  | 1.149   | 0.064 | 0.141        | —          |

Of these antibodies, those designated 3F and 8G, are such having the characteristics of the antibodies of the present invention, i.e. specific for the gp120/anti V3 loop complex and bind at very low affinity to the M77 mAb and gp120$_{IIIB}$.

What is claimed is:

1. An antigenic epitope which is a member of a group consisting of:
    (i) an epitope consisting of a sequence in a member of a binding couple, which becomes substantially more accessible to antibodies or resumes a new conformation after binding of the two members to one another,
    (ii) an epitope consisting of two or more sequences in a member of a binding couple which upon binding of the two members, become closely associated to form an antigenic epitope, and
    (iii) an epitope consisting of two or more sequences, at least one being in one member of a binding couple, and at least one other being in the other member of the binding couple and upon binding of the two members, said two or more amino acid sequences become closely associated with one another to form an antigenic epitope;

said antigenic epitope being immunogenic.

2. An epitope according to claim 1, being revealed after antibody-antigen or ligand receptor binding.

3. An epitope according to claim 2, being revealed after virus or viral particle-receptor binding.

4. An epitope according to claim 3, being revealed after HIV or gp120-CD4 binding.

5. An epitope according to claim 4 that binds to a monoclonal antibody produced by the CG-10 hybridoma deposited with the European Collection of Animal Cell Culture (ECACC) under the accession No. 93020415.

6. An epitope according to claim 5 being the anti-idiotype of a mAb produced by the CG-10 hybridoma.

7. An epitope according to claim 4, consisting of a sequence in the gp120 protein.

8. An epitope according to claim 2, being revealed after binding of gp120 to an anti-gp120 antibody.

9. An epitope according to claim 8, consisting of a sequence present in the gp120 protein.

10. An epitope according to claim 2, wherein the ligand is selected from the group consisting of hormones, neurotransmitters and toxins.

* * * * *

UNITED STATES PATENT AND TRADEMARK OFFICE
CERTIFICATE OF CORRECTION

PATENT NO.    : 6,143,876
DATED         : November 7, 2000
INVENTOR(S)   : Jonathan M. Gershoni It is certified that error appears in the above-identified patent and that said Letters Patent is hereby corrected as shown below:

Column 1,
Line 13, before "Field of the Invention", insert the following new section:
--            GOVERNMENT LICENSE RIGHTS
        The U.S. Government has a paid-up license in this invention and the right in limited circumstances to require the patent owner to license others on reasonable terms as provided for by the terms of Contract No. DAMD17-91-C-1091 awarded by the U.S. Army Medical Research and Development Command. --

Column 2,
Line 38, delete "inding" and insert therefor -- binding --.

Column 4,
Line 14, delete "$20^0$" and insert therefor -- $20^6$ --.
Line 36, delete "imune" and insert therefor -- immune --.

Column 6,
Line 38, delete "baculavirus" and insert therefor -- baculovirus --.

Column 7,
Lines 34 and 35, delete "$20^s$" and insert therefor -- $10^8$ --.

Column 8,
Line 32, delete "mabs" and insert therefor -- mAbs --.

Column 9,
Lines 6 and 7, delete "1 $\mu$" and insert therefor -- 1 $\mu$g --.

Signed and Sealed this

Eleventh Day of February, 2003

JAMES E. ROGAN
*Director of the United States Patent and Trademark Office*